(12) United States Patent
Markelov

(10) Patent No.: US 6,395,229 B1
(45) Date of Patent: May 28, 2002

(54) HEADSPACE SAMPLING APPARATUS AND METHOD

(76) Inventor: Michael Markelov, 7276 Greenfield, Chesterland, OH (US) 44026

( * ) Notice: Subject to any disclaimer, the term of this patent is extended or adjusted under 35 U.S.C. 154(b) by 0 days.

(21) Appl. No.: 09/575,278

(22) Filed: May 22, 2000

Related U.S. Application Data

(60) Provisional application No. 60/135,546, filed on May 24, 2000.

(51) Int. Cl.$^7$ ................................................. G01N 7/00
(52) U.S. Cl. ........................... 422/83; 422/68.1; 422/50; 436/43; 436/47
(58) Field of Search ........................ 436/83, 181, 133, 436/61; 422/83, 99, 100; 73/864.91, 863, 864; 95/82, 90; 96/101, 108, 397

(56) References Cited

U.S. PATENT DOCUMENTS

| | | | | |
|---|---|---|---|---|
| 3,849,070 A | * | 11/1974 | Garza et al. ................. | 436/133 |
| 3,915,646 A | * | 10/1975 | Harris et al. ................ | 324/71.1 |
| 4,452,067 A | * | 6/1984 | Ahlstrom et al. .......... | 73/23.38 |
| 5,441,700 A | * | 8/1995 | Markelov .................... | 422/83 |
| 5,644,068 A | * | 7/1997 | Okamoto et al. ........... | 73/23.32 |
| 5,693,538 A | * | 12/1997 | Capuano et al. ............. | 436/181 |
| 5,792,423 A | * | 8/1998 | Markelov ..................... | 422/83 |
| 5,932,482 A | * | 8/1999 | Markelov .................... | 436/181 |
| 6,146,895 A | * | 11/2000 | Green et al. .................. | 436/47 |
| 6,277,649 B1 | * | 8/2001 | Markelov .................... | 436/181 |

* cited by examiner

*Primary Examiner*—Jill Warden
*Assistant Examiner*—Brian J. Sines
(74) *Attorney, Agent, or Firm*—Christopher L. Parmelee; Walker & Jocke LPA; Ralph E. Jocke

(57) ABSTRACT

A headspace sampling apparatus (10) operates to provide a sample of a vapor phase of a substance being analyzed under conditions of thermodynamic equilibrium. The substance is held in a vial (14). The vapor phase of the substance (18) is moved through a sample loop (34) between a first variable volume chamber (22) and a second variable volume chamber (40). A constant volume and temperature is maintained within the variable volume chambers, the sample loop and the headspace of the vial. An aliquot of the equilibrated vapor in the sample loop is passed to an analytical instrument (54) for analysis. The sample is obtained under conditions in which the sampling process does not affect the makeup of the sample because thermodynamic equilibrium is maintained.

26 Claims, 2 Drawing Sheets

HEADSPACE SAMPLING APPARATUS AND METHOD

This application claims the benefit of U.S. Provisional Application No. 60/135,546, filing date May 24, 2000.

TECHNICAL FIELD

This invention relates to devices and methods for chemical analysis of materials. Specifically this invention relates to headspace analysis, and apparatus and methods used to increase sensitivity and repeatability in conducting headspace analysis.

BACKGROUND ART

Headspace analysis is a relatively new technique which enables the sampling of a vapor phase of a sample with an analytical instrument. Headspace sampling ensures that only volatile materials are delivered for analysis. For example when the analytical instrument used is a gas chromatograph, headspace sampling assures that only volatile species that can be eluted from a column of a gas chromatograph will be introduced into the instrument.

In headspace sampling a volatile non-vapor phase of a substance being analyzed, which may be either liquid or solid attains equilibrium with a vapor phase of the substance within a sealed vial. Equilibrium is established when the non-vapor phase of the substance in the vial no longer changes so that the total quantity of the vapor and non-vapor phases remains constant. Often a syringe is used to retrieve a small sample of the vapor for analysis. The retrieved vapor is then introduced into an analytical instrument. Headspace technology is advantageous over conventional direct sample injection techniques because it allows only vapor to enter the analytical instrument. This is advantageous because it reduces the chance of contamination or damage to the analytical instrument due to introduction of unevaporated sample material. Because the sample is in vapor form, greater sample volumes may be supplied to the instrument. Increased sample size generally results in increased sensitivity.

Samples of headspace vapor may be extracted from a sample vial using a number of other techniques. Such techniques often involve equilibrating the vapor and non-vapor phase of a substance for analysis within a closed vial. A sample needle is moved to pierce a septum bounding the headspace in the vial. As a result a fluid passage through the needle is in fluid communication with the vapor phase of the sample in the headspace. To extract the headspace sample it is usually necessary to first pressurize the headspace with a suitable gas.

After the headspace has been pressurized the pressure is released allowing the sample material to pass out of the vial and into an analytical instrument or other device for collecting or analyzing the sample. Techniques for extracting headspace vapor from a vial are shown in U.S. Pat. No. 5,441,700 the disclosure of which is incorporated by reference as if fully rewritten herein.

A drawback associated with conventional techniques for the extraction of sample vapor from a headspace vial is that variations in pressure must be achieved to extract the sample material. Such variations in pressure often change the equilibrium conditions between the vapor phase and the non-vapor phase of the substance being analyzed. Changes in equilibrium may change the makeup of the headspace vapor. Such changes which result from the sampling process often impact the results in ways that are undesirable.

Thus there exists a need for a headspace sampling apparatus and method which minimizes the effects of the sampling process on the constituents in the sample and which increases sample volumes which may be delivered and/or analyzed by an analytical instrument.

OBJECTS OF INVENTION

It is an object of the present invention to provide a sampling apparatus which achieves the sampling of headspace vapors while minimizing the disturbance of thermodynamic equilibrium.

It is a further object of the present invention to provide a sampling apparatus with improved sensitivity.

It is a further object of the present invention to provide a sampling apparatus which increases sample volumes which may be analyzed by an analytical instrument.

It is a further object of the present invention to provide an improved method of sampling materials for analysis.

It is a further object of the present invention to provide a method of sampling that reduces the effects of pressure changes on a headspace sample.

It is a further object of the present invention to provide a method of sampling that may achieve greater sample size.

It is a further object of the present invention to provide a method of sampling which achieves increased sensitivity.

It is a further object of the present invention to provide a method of sampling under conditions of thermodynamic equilibrium.

Further objects of the present invention will be made apparent in the following Best Modes for Carrying Out Invention and the appended claims.

The foregoing objects are accomplished in an exemplary embodiment of the invention by a system and method in which a material to be analyzed is held in a generally sealed vial. The vial is positioned in an equilibration chamber. At least two needles or similar fluid passages extend into the otherwise sealed vial. The needles extend into the headspace which holds a vapor phase of the material being analyzed which is generally above a non-vapor phase of the material.

One of the needles is in fluid communication with a first variable volume chamber. The second needle is in fluid communication with a second variable volume chamber similar to the first variable volume chamber. The fluid connections between the headspace of the vial and either the first or the second variable volume chamber includes a sample loop which is in operative connection with, or which may be connected, to an analytical instrument.

In operation of the exemplary embodiment the volumes of the first and second variable volume chambers are varied periodically and in a controlled synchronized manner. The volume of the first chamber is reduced as the volume of the second chamber is correspondingly increased. As this occurs vapor flows through the headspace of the vial, through the sample loop and into the chamber whose volume is increasing. Thereafter the flow is reversed such that the volume of the other chamber begins to increase while the volume of the other chamber decreases. As this occurs vapor flows in the opposite direction through the headspace and the sample loop. Because the volumes of the headspace, the sample loop and the first and second chambers remain constant, thermodynamic equilibrium is maintained in the headspace of the vial while the vapor phase of the sample is passed through the sample loop.

The vapor phase sample in the sample loop is analyzed through use of an analytical instrument. This may be accomplished for example, by switching a valve such that the material in the sample loop is passed to a gas chromatograph. Alternatively the sample loop may include sensors such as optical cells of spectrophotometers, semiconductor aroma sensors or other suitable sensors for analysis of the constituents in or the properties of the vapor phase of the substance.

BEST MODES FOR CARRYING OUT INVENTION

Figure 1:
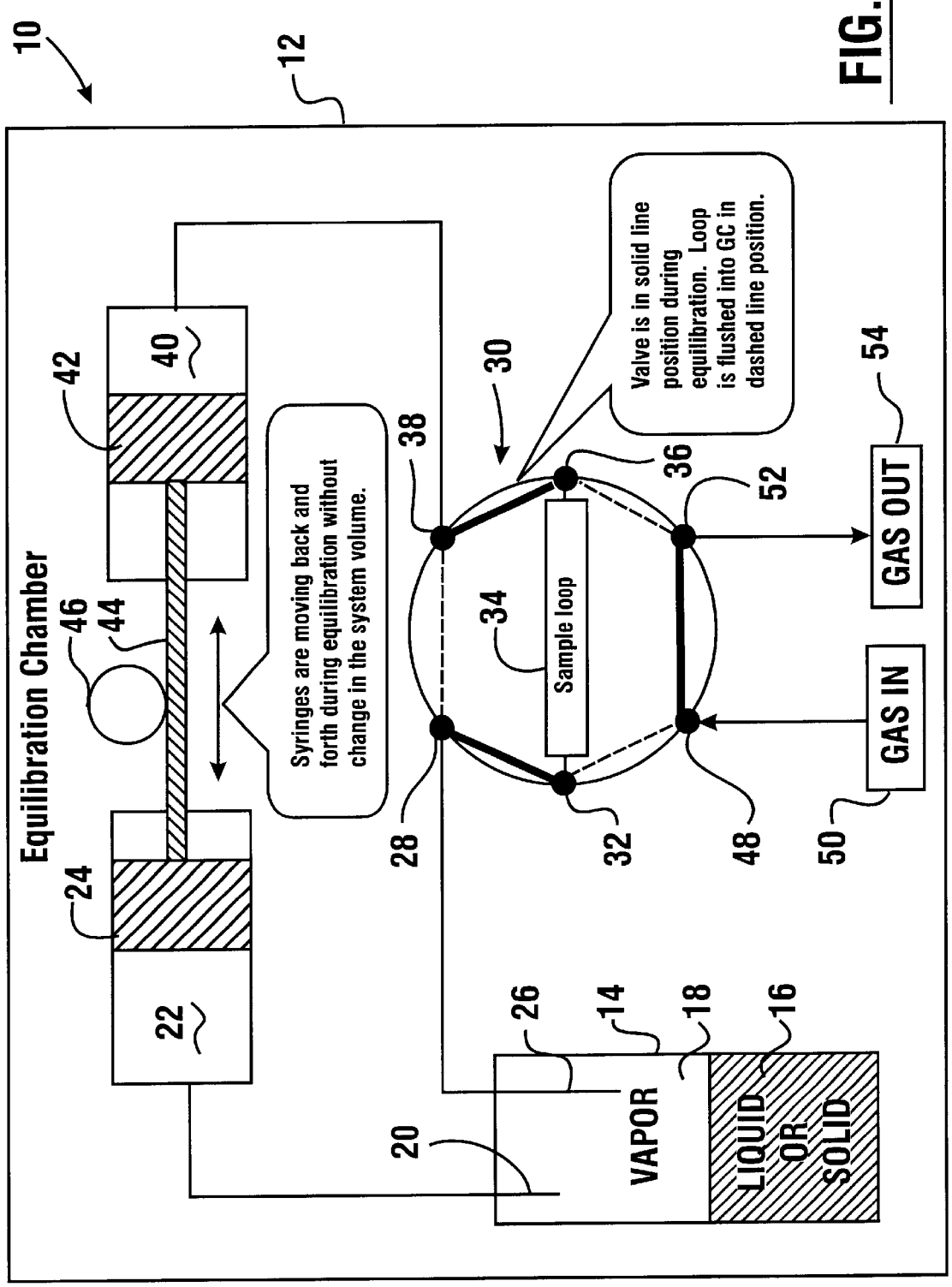
FIG. 1 is a schematic view of a headspace sampling apparatus in a condition in which a vapor phase of a sample is passed through a sample loop.

Referring now to the drawings and particularly to FIG. 1, there is shown therein a schematic view of a headspace sampling apparatus of an exemplary embodiment generally indicated 10. Generally the components of the apparatus are positioned in an equilibration chamber generally indicated 12. The equilibration chamber is generally maintained at environmental conditions which facilitate equilibrium between the vapor phase and the non-vapor vapor phase of the material being analyzed. In many cases the equilibration chamber is maintained at an elevated temperature. Of course in other embodiments, other temperature, pressure or atmospheric conditions may be controlled within the equilibration chamber.

A material to be analyzed is held in a generally closed headspace vial 14. As shown in FIG. 1, vial 14 holds a sample material which has a non-vapor phase 16. The non-vapor phase may be a liquid or solid portion of the sample. A vapor phase of the sample 18 is confined in the headspace vial 14 above the non-vapor phase of the sample.

A first sample needle 20 extends into the vapor phase of the substance being analyzed. First sample needle 20 may extend into the vial through a resilient septum or other member which bounds the headspace in a manner similar to that described in the incorporated disclosure of U.S. Pat. No. 5,441,700. First sample needle 20 includes a fluid passage therethrough and is in fluid connection with a first variable volume chamber 22. First variable volume chamber 22 is bounded by a first movable piston 24.

A second sample needle 26 like first sample needle 20, extends in the vapor phase of the sample. Second sample needle 26 is in fluid communication with a port 28 of a six port valve 30. When valve 30 is in the first condition shown in FIG. 1 port 28 is in fluid connection with a port 32 of the valve. Port 32 is in fluid connection with a sample loop 34. In this exemplary embodiment, sample loop 34 includes a fluid passage for the vapor phase of the sample material. In other embodiments the sample loop may include other features such as a trap or other material collection apparatus. In further alternative embodiments the sample loop may include sensors or analytical devices.

As shown in FIG. 1 sample loop 34 in the first condition of valve 30 is in fluid communication with a port 36 of the valve. Port 36 is in fluid communication through valve 30 with a port 38.

Port 38 in the first condition of valve 30 shown in FIG. 1 is in fluid connection with a second variable volume chamber 40. Second variable volume chamber 40 is bounded by a second movable piston 42. In the exemplary embodiment of the invention first piston 24 and second piston 42 are operatively connected by a connecting member 44. Connecting member constrains movement of pistons 24 and 42 so that they move in synchronized relation. As a result when piston 24 moves to the left as shown in FIG. 1, the volume of first variable volume chamber 22 decreases as the volume of second variable volume chamber 40 increases at the same rate and by the same amount. Likewise when pistons 24 and 42 move to the right as shown in FIG. 1 the volume of first variable volume chamber 22 increases as the volume of second variable volume chamber 40 decreases. A drive schematically indicated 46 is operatively connected to member 44 and is selectively operative to move pistons 24 and 42 to move with a reciprocating motion. In an exemplary embodiment of the invention, variable volume chambers 22 and 40 comprise syringes with plungers that are operatively driven in a reciprocating motion with a drive. Of course in other embodiments other devices and actuators may be used.

As shown in FIG. 1 in the first condition of valve 30, a port 48 of the valve is in communication with a supply of carrier gas schematically indicated 50. In this exemplary embodiment the carrier gas is preferably gas of a type that is suitable for transporting the vapor phase of the substance being analyzed into an analytical instrument. A port 52 of valve 30 in the first condition of the valve is in fluid communication with port 48. Port 52 is in fluid communication with an analytical instrument schematically indicated 54. In this exemplary embodiment the analytical instrument may be a gas chromatograph. Of course in other embodiments of the invention other analytical instruments may be used.

Figure 2:
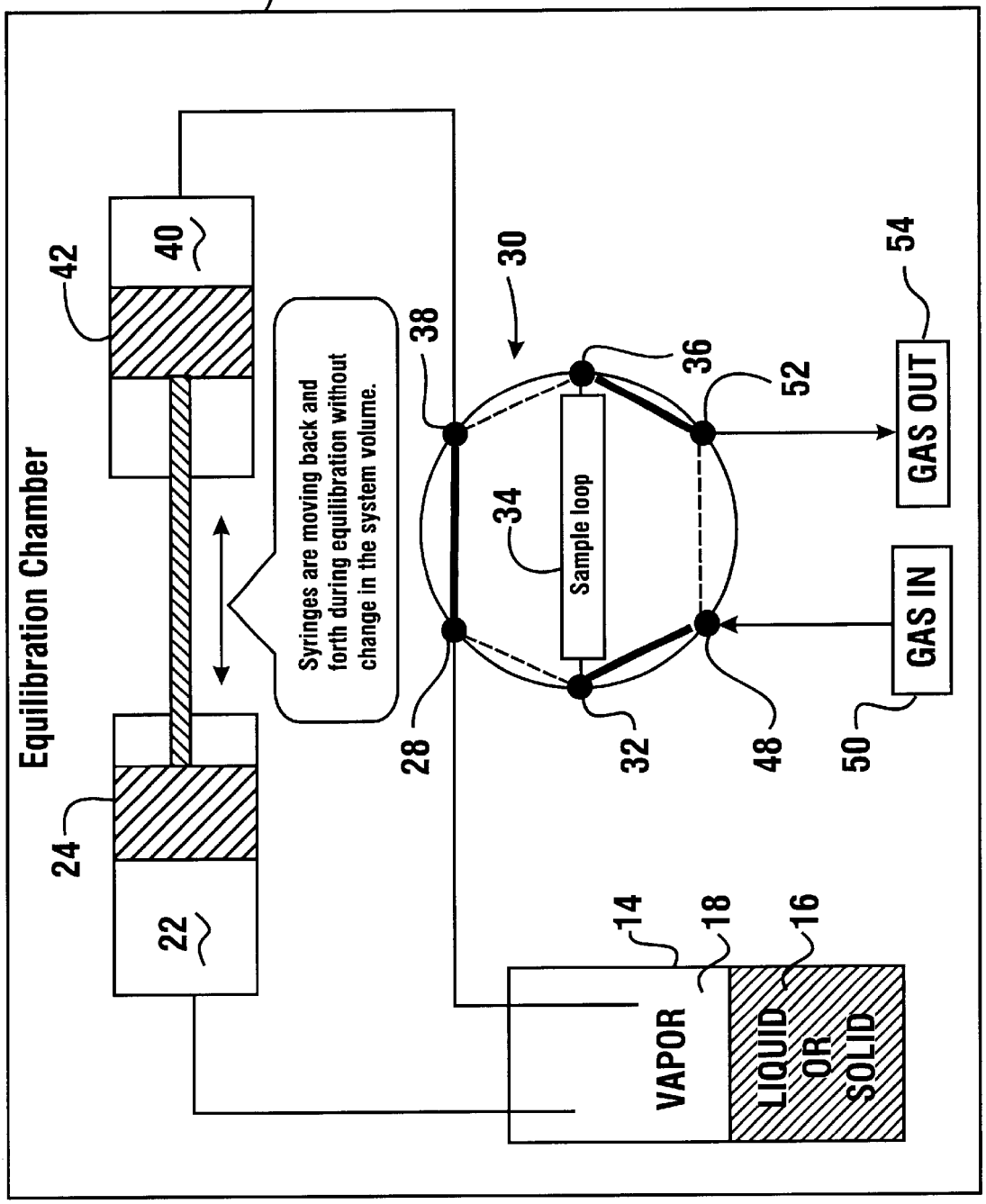
FIG. 2 is a schematic view of a headspace sampling apparatus shown in FIG. 1 delivering the vapor phase of the sample from the sample loop to an analytical instrument.

In operation of the sampling apparatus the pistons 24 and 42 are reciprocated in a back and forth motion responsive to operation of the drive 46. This causes the volume of chamber 22 to cyclically decline and then increase as the volume of chamber 40 correspondingly increases and declines. The fluid flow between chamber 22 and chamber 40 passes through the headspace of the vial 14 where the vapor phase of the sample is generated. As a result the vapor phase of the material to be analyzed fills the chambers 22 and 40 as well as the sample loop 34. This vapor phase of the sample is generated under conditions of thermodynamic equilibrium due to the maintenance of a constant total volume in chambers 22 and 40 and the consistent environmental conditions in the equilibration chamber 12. The equilibrated vapor sample in the sample loop is analyzed in the exemplary embodiment by changing the condition of valve 30 to a second condition shown schematically in FIG. 2. When the valve 30 is changed to the second condition port 48 is placed in fluid communication through the valve 30 with port 32. This causes an aliquot of the equilibrated vapor in the sample loop to be moved by the carrier gas through port 52 which is in fluid communication with port 36 of the valve in the second condition. The sample vapor is then passed from port 52 into the analytical instrument 54. During this time that the sample of equilibrated vapor in the sample loop is passed to the instrument ports 28 and 38 are maintained in fluid communication through the valve 30.

As can be appreciated the vapor in the sample loop is acquired under conditions of thermodynamic equilibrium. As a result the sampling process does not impact the concentrations of the constituents which make up the vapor phase of the sample in vial 14. This enables the headspace sampling apparatus made in accordance with the teachings of the invention to have improved sensitivity and repeatability.

While the exemplary embodiment shows the sample loop 34 operating as a collection conduit for an aliquot of the sample vapor, in other embodiments the sample loop may include additional devices or sensors. For example the sample loop may include a trap which adsorbs particular materials from the sample vapor. The materials adsorbed may then be released selectively into an appropriate analytical instrument. Alternatively the sample loop may include sensors for sensing particular substances within the sample vapor. Such sensors may include for example optical cells of spectrophotometers, semiconductor aroma sensors or other sensing devices. As can be appreciated, in embodiments of the invention a sensor in the sample loop may be repeatedly and continuously exposed to the vapor phase of the sample as the sample flows across the sensor in the sample loop. These techniques may further enhance the analytical capabilities of the instrument. Further or additional features and methods for utilizing the principles of the present invention will be apparent to those skilled in the art for the preceding description.

Thus the new headspace sampler apparatus and method of the present invention achieves the above stated objectives, eliminates difficulties encountered in the use of prior devices and systems, solves problems and attains the desirable results described herein.

In the foregoing description certain terms have been used for brevity, clarity and understanding, however no unnecessary limitations are to be implied therefrom because such terms are used for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means known to those skilled in the art to be capable of performing the recited function, and shall not be limited to the structures shown herein or mere equivalents thereof.

Having described the features, discoveries and principles of the invention, the manner in which it is constructed and operated, and the advantages and useful results attained; the new and useful structures, devices, elements, arrangements, parts, combinations, systems, equipment, operations, methods and relationships are set forth in the appended claims.

I claim:

1. A headspace sampling sampling apparatus comprising:
a vial, wherein the vial includes a headspace, wherein when a material to be analyzed is placed within the vial, the headspace is operative to hold a portion of the vapor phase of the material;
at least two fluid passages in fluid communication with the headspace of the vial; and at least two chambers, wherein a first one of the fluid passages is operative to be in fluid communication with a first one of the chambers, and wherein a second one of the fluid passages is operative to be in fluid communication with a second one of the chambers, wherein the first chamber includes a first variable volume, and wherein the second chamber includes a second variable volume, wherein the first chamber and the second chamber are operative to respond to at least one drive to simultaneously decrease the first variable volume of the first chamber and increase the second variable volume of the second chamber, whereby changes to the first variable volume of the first chamber and the second variable volume of the second chamber are operative to urge the portion of the vapor phase to move from the headspace of the vial through the second fluid passages;
the apparatus further comprising a sample loop that is operative to be in fluid communication with the first and second fluid passages;
and wherein as the first and second variable volumes change, the first and second chambers are operative to urge a portion of the vapor phase of the material to flow from the headspace of the vial to the sample loop.

2. The headspace sampling apparatus according to claim 1, wherein as the first variable volume decreases by a first amount of volume, the second variable volume increases by a second amount of volume that corresponds to the first amount of volume.

3. The headspace sampling apparatus according to claim 1, wherein the first amount of volume is about equal to the second amount of volume, and wherein the first variable volume is operative to change simultaneously with the second variable volume.

4. The headspace sampling apparatus according to claim 1, wherein as the second variable volume decreases by a third amount of volume, the first variable volume increases by a fourth amount of volume, the first and second chambers are operative to urge materials that are present in the sample loop to flow from the sample loop to the headspace of the vial.

5. The headspace sampling apparatus according to claim 1, wherein the total volume of the headspace, the sample loop, the first chamber and the second chamber remains generally constant, whereby thermodynamic equilibrium is maintained in the headspace of the vial as the vapor phase of the material flows through the sample loop.

6. The headspace sampling apparatus according to claim 1, wherein the sample loop is in switchable connection with a gas chromatograph.

7. The headspace sampling apparatus according to claim 1, further comprising a switching valve, wherein the switching valve is operative to place the sample loop in fluid communication with an analytical instrument.

8. The headspace sampling apparatus according to claim 5, further comprising a carrier gas supply in operative connection with the switching valve, wherein the switching valve is farther operative to place the sample loop in fluid communication with the carrier gas supply, wherein a carrier gas from the carrier gas supply is enabled to flow through the sample loop so as to urge the vapor phase of the material to flow from the sample loop to the analytical instrument.

9. The headspace sampling apparatus according to claim 1, wherein the sample loop includes sensors operative to analyze properties of the vapor phase of the material.

10. The headspace sampling apparatus according to claim 1, wherein the fluid passages include needles that extend through a septum which bounds the vial.

11. The headspace sampling apparatus according to claim 1, wherein the sample loop further includes a trap for collecting substances.

12. The headspace sampling apparatus according to claim 1, further comprising a connection member, wherein the first chamber includes a first piston, wherein the second chamber includes a second piston, wherein the connection member is in operative connection between the first piston and the second piston, wherein the connection member is operative to synchronize the movements of the first piston and the second piston.

13. The headspace sampling apparatus according to claim 12, further comprising the drive in operative connection with the connection member wherein the drive is selectively operative to move the first piston and the second piston in a reciprocating motion.

14. The headspace sampling apparatus according to claim 12, wherein each of the chambers are comprised of syringes, wherein each of the pistons are comprised of syringe plungers.

15. The headspace sampling apparatus according to claim 1, wherein the vial is in operative connection with an equilibration chamber, wherein the equilibration chamber is operative to generally maintain an equilibrium between the vapor phase of the material and a non-vapor phase of the material being analyzed.

16. The headspace sampling apparatus according to claim 15, wherein the equilibration chamber is operative to maintain the vial at an elevated temperature.

17. A headspace sampling method comprising:

receiving a material in a vial;

generating a vapor phase of the material in a headspace of the vial, wherein the headspace includes a first passageway and a second passageway, wherein the first passageway is in fluid communication between the headspace and a first chamber and the second passageway is in fluid communication between the headspace and a second chamber; and urging a portion of the vapor phase to flow through the second passageway into a sampling loop in fluid communication with said second passageway and said second chamber, including simultaneously decreasing a first volume of the first chamber by a first amount of volume and increasing a second volume of the second chamber by a second amount of volume that corresponds to the first amount of volume.

18. A head space sampling method according to claim 17, further comprising maintaining a total volume of the headspace, the sample loop, the first chamber, and the second chamber at a generally constant level.

19. A head space sampling method according to claim 18, further comprising analyzing the portion of the vapor phase.

20. A head space sampling method according to claim 18, further comprising urging the portion of the vapor phase to flow from the sample loop to an analytical instrument.

21. A head space sampling method according to claim 18, further comprising activating a switch to place the sample loop in fluid communication with an analytical instrument.

22. A head space sampling method according to claim 18, further comprising urging the portion of the vapor phase to flow from the sample loop to an analytical instrument with a carrier gas.

23. A head space sampling method according to claim 18, wherein both the first and second chambers each include a piston, and further comprising moving the pistons in a synchronized reciprocating motion.

24. A head space sampling method according to claim 18, further comprising maintaining an equilibrium between the vapor phase of the material and a non-vapor phase of the material being analyzed.

25. A head space sampling method according to claim 24, further comprising maintaining the vial at a generally constant elevated temperature.

26. A head space sampling method according to claim 18, further comprising collecting a substance in a trap in fluid communication with the sample loop.

* * * * *

UNITED STATES PATENT AND TRADEMARK OFFICE
CERTIFICATE OF CORRECTION

PATENT NO. : 6,395,229 B1
DATED : May 28, 2002
INVENTOR(S) : Michael Markelov

It is certified that error appears in the above-identified patent and that said Letters Patent is hereby corrected as shown below:

Column 3,
Line 27, replace "non-vapor vapor phase" with -- non-vapor phase --.

Column 6,
Line 39, replace "claim 5" with -- claim 7 --.
Line 41, replace "farther" with -- further --.

Signed and Sealed this

Eighth Day of October, 2002

*Attest:*

*Attesting Officer*

JAMES E. ROGAN
*Director of the United States Patent and Trademark Office*